(12) United States Patent
Garcia et al.

(10) Patent No.: US 6,235,909 B1
(45) Date of Patent: May 22, 2001

(54) **PREPARATION OF IS-[1A,2B,3B,4A(S*)]-4-[7-[[1-(3-CHLORO-2-THIENYL)METHYL] AMINO]-3H-IMIDAZO [4,5-B]PYRIDIN-3-YL]-N-ETHYL-2,3-DIHYDROXYCYCLOPENTANECARBOXAMIDE**

(75) Inventors: Herve Garcia, Communay; Patrick Leon, Tassin La Demi Lune, both of (FR); Benoit J. Vanasse, Collegeville, PA (US)

(73) Assignee: Aventis Pharmaceuticals Products Inc., Bridgewater, NJ (US)

( * ) Notice: Subject to any disclaimer, the term of this patent is extended or adjusted under 35 U.S.C. 154(b) by 0 days.

(21) Appl. No.: 09/627,657

(22) Filed: Jul. 28, 2000

Related U.S. Application Data

(62) Division of application No. 09/233,591, filed on Jan. 19, 1999, now Pat. No. 6,143,894, which is a continuation of application No. PCT/US97/21439, filed on Nov. 24, 1997.

(60) Provisional application No. 60/032,764, filed on Dec. 11, 1996, now abandoned.

(51) Int. Cl.$^7$ .................. C07D 213/00; C07D 213/62
(52) U.S. Cl. .................. 546/296; 546/290; 546/288
(58) Field of Search .................. 546/296, 290, 546/288

(56) References Cited

U.S. PATENT DOCUMENTS 6,143,743 * 11/2000 Wilde et al. .................. 514/234.2

* cited by examiner

Primary Examiner—Charanjit S. Aulakh
(74) Attorney, Agent, or Firm—Irving Newman

(57) ABSTRACT

This invention is directed to methods for the preparation of [1S-[1a,2b,3b,4a(S*)]]-4-[7-[[-(3-chloro-2-thienyl)methyl] propyl]amino]-3 H-imidazo[4,5-b]pyridin-3-yl]]-N-ethyl-2, 3-dihydroxycyclopentanecarboxamide, methods for the preparation of intermediates thereto, and to said intermediates themselves.

2 Claims, No Drawings

PREPARATION OF IS-[1A,2B,3B,4A(S*)]-4-[7-[[1-(3-CHLORO-2-THIENYL)METHYL]AMINO]-3H-IMIDAZO [4,5-B]PYRIDIN-3-YL]-N-ETHYL-2,3-DIHYDROXYCYCLOPENTANECARBOXAMIDE

CROSS REFERENCE TO RELATED APPLICATIONS

This application is a divisional of U.S. patent application Ser. No. 09/233,591, filed Jan. 19, 1999, now U.S. Pat. No. 6,143,894 which is a continuation of International Patent Application No. PCT/US97/21439, filed Nov. 24, 1997, which, in turn, is a continuation of U.S. Ser. No. 60/032,764 filed Dec. 11, 1996, now abandoned.

BACKGROUND OF INVENTION

1. Field of the Invention

This invention is directed to methods for the preparation of [1S-[1a, 2b,3b,4a(S*)]]4-[7-[[1-(3-chloro-2-thienyl)methyl]propyl]amino]-3H-imidazo[4,5-b]pyridin-3-yl]-N-ethyl-2,3-dihydroxycyclopentanecarboxamide, i.e., Compound I,

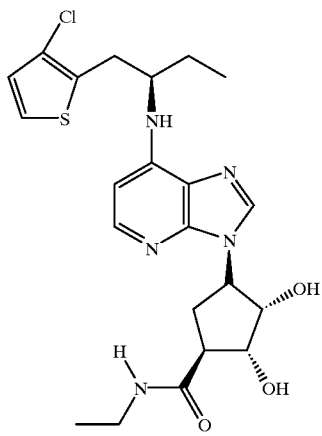

(I)

methods for the preparation of intermediates thereto, and to said intermediates themselves.

Compound I is useful as a cardiovascular agent, more particularly as an antihypertensive and anti-ischemic agent, as a cardioprotective agent which ameliorates ischemic injury or myocardial infarct size consequent to myocardial ischemia, and as an antilipolytic agent which reduces plasma lipid levels, serum triglyceride levels, and plasma cholesterol levels.

For example, U.S. Pat. No. 5,364,862 discloses Compound I and related compounds are useful as an antihypertensive and anti-ischemic agents, and U.S. Pat. No. 5,561,134 discloses their utility as cardioprotective and antilipolytic agents.

2. Reported Developments

Methods of preparing Compound I, related compounds and intermediates thereto have been disclosed by Spada et al. in U.S. Pat. No. 5,364,862. issued Nov. 15, 1994, and in U.S. Pat. No. 5,561,134.

The methods of preparation of the present invention offer improved yields, purity, ease of preparation and/or isolation of intermediates and final product, and more industrially useful reaction conditions and workability over previously disclosed methods of preparation.

SUMMARY OF THE INVENTION

This invention is directed to methods for the preparation of [1S-[1a,2b,3b,4a(S*)]]-4-[7-[[1-(3-chloro-2-thienyl)methyl]propyl]amino]-3H-imidazo[4,5-b]pyridin-3-yl]-N-ethyl-2,3-dihydroxycyclopentanecarboxamide, i.e., Compound I, methods for the preparation of intermediates thereto, and to said intermediates themselves.

DETAILED DESCRIPTION OF THE INVENTION

Preferred embodiments according to the invention are illustrated in Schemes I, II, III and IV.

Scheme I

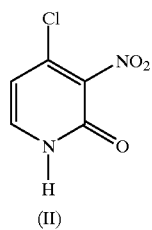

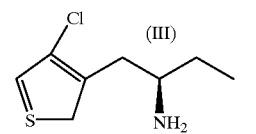

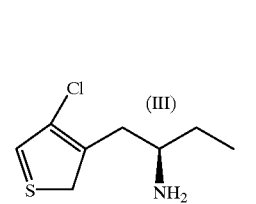

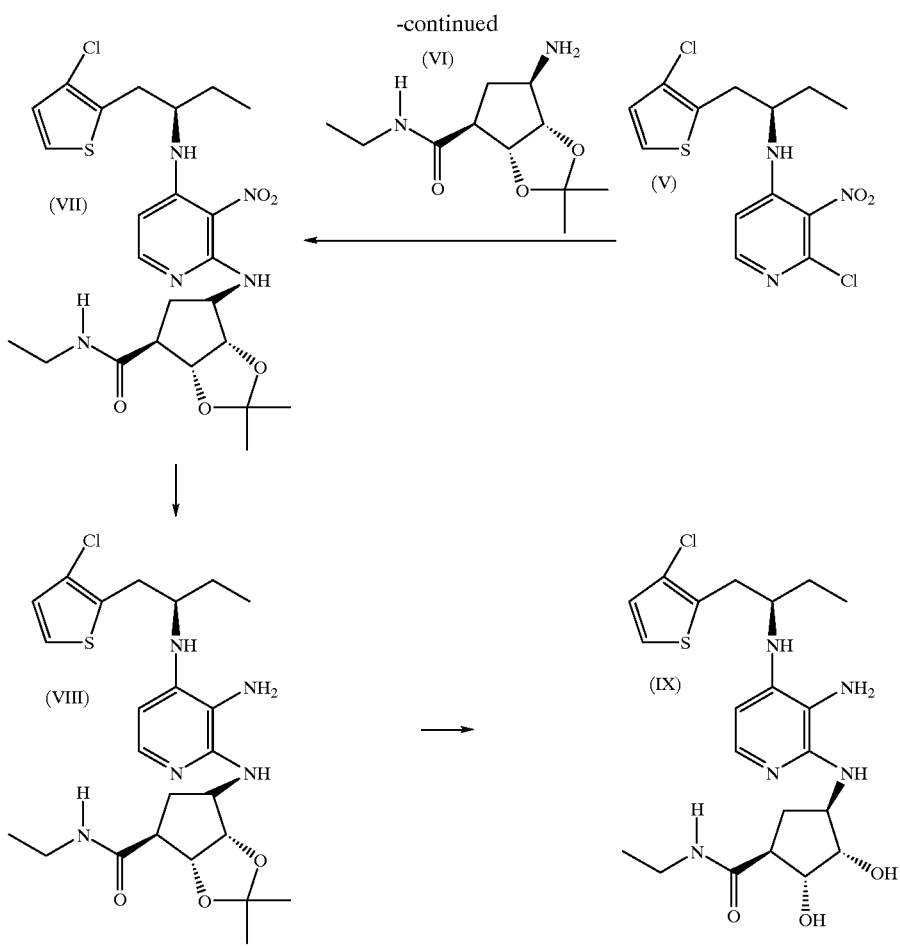
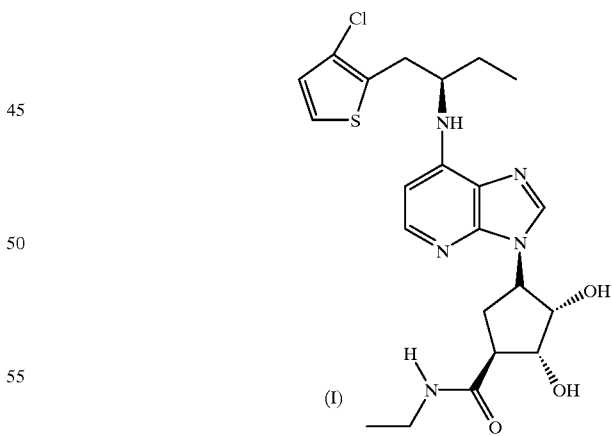
Scheme II
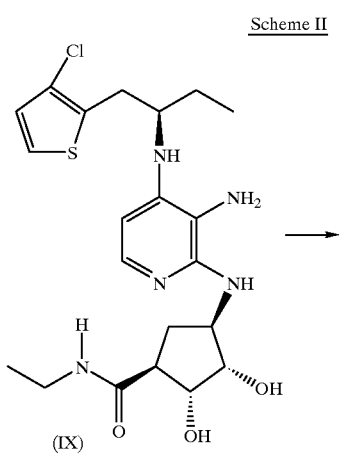
Scheme III
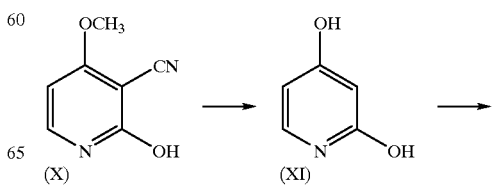

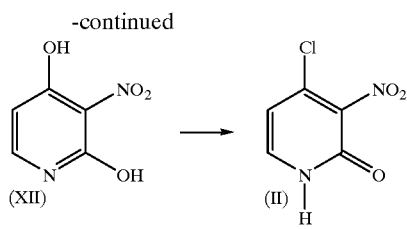

An embodiment according to the invention is directed to a method for preparing Compound I comprising reacting [1S-[1a,2b,3b,4a(S*)]]4-[[3-amino-4-[[1-[3-chloro-2-thienyl)methyl]propyl]amino]-2-pyridinyl]amino]-N-ethyl-2,3-dihydroxycyclopentanecarboxamide (Compound IX) with formamidine acetate, or with an orthoformate ester or dimethylformamide dimethyl acetal, optionally in the presence of a catalytic amount of an inorganic or organic acid. The reaction takes place preferably in an organic solvent, or mixture of organic solvents, water, or a mixture of an organic solvent or solvents and water. In a special embodiment of methods according to the invention, the reaction takes place preferably with formamidine acetate in n-butyl acetate. In another special embodiment of methods according to the invention, the reaction takes place preferably with triethyl orthoformate, in the presence of a catalytic amount of an inorganic or organic acid, preferably hydrochloric acid or camphorsulfonic acid.

A preferred embodiment according to the invention is directed to a method for preparing Compound I, preferably in a crystalline form, comprising the steps of forming the free base of Compound IX from a dihydrochloride salt thereof, followed by reacting said free base with formamidine acetate, said steps being effected in a concatenated manner without a necessity for interim isolation and purification of the free base of Compound IX.

A more preferred embodiment according to the invention is directed to a method for preparing Compound I in a crystalline form comprising reacting the dihydrochloride salt of Compound IX with formamidine acetate, without initial formation of the free base of Compound IX.

Another embodiment of the invention is directed to a method for preparing said Compound IX comprising hydrolyzing [3aR-[3aa,4a,6a(R*),6aa]]-6-[[3-amino4-[[1-[(3-chloro-2-thienyl)methyl]propyl]amino]-2-pyridinyl]amino]-N-ethyltetrahydro-2,2-dimethyl-4H-cyclopenta-1,3-dioxole-4-carboxamide (Compound VIII), preferably in the presence of an organic solvent or a mixture of organic solvents, and an aqueous mineral or organic acid. Examples of suitable organic solvents include methanol, ethanol, isopropanol, ethyl acetate, toluene, tetrahydrofuran, tetrahydropyran, and dioxan. In a special embodiment of methods according to the invention, the preferred solvent is methanol, or a mixture of toluene and isopropanol. In special embodiments of methods according to the invention, a preferred mixture to effect the hydrolysis of Compound VIII to Compound IX is tetrahydrofuran and aqueous hydrochloric acid, methanol, ethanol, or isopropanol and aqueous hydrochloric acid, or ethyl acetate or ethyl acetate and isopropanol and aqueous hydrochloric acid.

Another embodiment of the invention is directed to a method for preparing said Compound VIII comprising reducing [3aR-[3aa,4a,6a(R*),6aa]]-6-[[4-[[1-[(3-chloro-2-thienyl)methyl]propyl]amino]-3-nitro-2-pyidinyl]amino]-N-ethyltetrahydro-2,2-dimethyl-4H-cyclopenta-1,3-dioxole-4-carboxamide (Compound VII), preferably in the presence of an organic solvent or a mixture of an organic solvent and water. Examples of suitable organic solvents include methanol, ethanol, isopropanol, ethyl acetate, tetrahydrofuran, tetrahydropyran, and dioxan. In a special embodiment of methods according to the invention, the preferred solvent is methanol.

The reduction takes place preferably at a temperature range from about 2° C. to about 90° C.; more preferably at reflux of the system in which the reduction is taking place. In a special embodiment of methods according to the invention, the preferred temperature is about 65°, or reflux of the reduction system taking place in methanol.

The reduction of Compound VII to Compound VIII takes place in the presence of reducing agents known in the art or as described herein. Reducing agents which are suitable for the reduction include potassium borohydride in the presence of copper (I) chloride, iron and aqueous hydrochloric acid, zinc and calcium chloride platinum on carbon or palladium on carbon in the presence of hydrogen, platinum on carbon in the presence of ammonium formate, zinc powder in the presence of ammonium acetate, and platinum on sulfided carbon in the presence of ammonium formate. In special embodiments of methods according to the invention, a preferred reducing agent is platinum on water wet carbon, or zinc powder in the presence of a species capable of transferring hydrogen to the nitro group to be reduced, preferably ammonium acetate, or platinum on carbon in the presence of hydrogen.

Another embodiment of the invention is directed to a method for preparing said Compound VII comprising reacting (R)-2-chloro-N-[1-[(3-chloro-2-thienyl)methyl]propyl]-3-nitro-4-pyridinamine (Compound V) with 2R,3S-isopropylidenedioxy-4R-amino-1S-ethylaminocarbonylcyclopentane (Compound VI), preferably in the presence of an aprotic organic solvent. Aprotic organic solvents which are suitable for the reaction include aprotic organic ethers, aromatic hydrocarbons, heteroaromatic hydrocarbons, aliphatic hydrocarbons and aprotic organic amides. In a special embodiment of methods according to the invention, a preferred organic solvent is toluene.

According to the invention, the reaction of Compound V with Compound VI takes place in the presence of a base. Bases which are suitable for the reaction include aqueous alkali metal hydroxides, aqueous alkali metal carbonates, aqueous alkali metal bicarbonates, and aprotic organic amines. In a special embodiment of methods according to the invention, a preferred base is potassium carbonate.

Another embodiment of the invention is directed to a method for preparing said Compound V comprising replacing the hydroxyl moiety of (R)-N-[1-[(3-chloro-2-thienyl)methyl]propyl]-2-hydroxy-3-nitro-4-pyridinamine (Compound IV) with a chloro group, preferably in the presence of an aprotic organic solvent. Aprotic organic solvents which are suitable for the reaction include aprotic organic ethers, aromatic hydrocarbons, heteroaromatic hydrocarbons, aliphatic hydrocarbons and aprotic organic amides. In a special embodiment of methods according to the invention, a preferred organic solvent is toluene. Agents which are suitable to effect the replacing include oxalyl chloride, phosphorus trichloride, phosphorus pentachloride, thionyl chloride and phosphorus oxychloride. In a special embodiment of methods according to the invention, the preferred agent is phosphorus oxychloride.

Another embodiment of the invention is directed to a method for preparing said Compound IV comprising reacting 4-chloro-3-nitropyridin-2(1H)-one (Compound II) with (R)-3-chloro-a-ethyl-2-thiopheneethaniamine (Compound III), preferably in the presence of an organic solvent or mixture of organic solvents, water or a mixture of organic solvent or solvents and water. Examples of suitable organic solvents include methanol, ethanol, isopropanol, ethyl acetate, tetrahydrofuran, tetrahydropyran, and dioxan. Examples of preferred solvents include methanol, ethanol, isopropanol, and a mixture of methanol, ethanol or isopropanol and water.

According to the invention, the reaction of Compound II with Compound III takes place in the presence of a base. Bases which are suitable for the reaction include aqueous alkali metal hydroxides, aqueous alkali metal carbonates, aqueous alkali metal bicarbonates, and aprotic organic amines. In a special embodiment of methods according to the invention, a preferred base is N,N-diisopropylethylamine.

Another embodiment of the invention is directed to a method for preparing said Compound II comprising reacting 4-hydroxy-3-nitro-2(1H)-pyridone (Compound XII) with phosphorus oxychloride or thionyl chloride, preferably phosphorus oxychloride, in the presence of an organic solvent, and in the presence of a base. Organic solvents which are suitable for the reaction include aprotic organic ethers, aromatic hydrocarbons, heteroaromatic hydrocarbons, aliphatic hydrocarbons, halogenated hydrocarbons and aprotic organic amides. Examples of suitable organic solvents include toluene, methyl t-butyl ether, dimethylformamide, ethyl acetate, butyl acetate, 1-methyl-2-pyrrolidinone, chloroform, and dichloromethane. In a special embodiment of methods according to the invention, a preferred organic solvent is toluene. In a special embodiment of methods according to the invention a preferred base is is N,N-diisopropylethylamine.

Another embodiment of the invention is directed to a method for preparing Compound XII comprising hydrolyzing and decarboxylating 2-hydroxy-3-cyano4-methoxy pyridine to give 2,4-dihydroxypyridine, followed by nitration of said 2,4-dihydroxypyridine. In a special embodiment of methods according to the invention, said hydrolyzing, decarboxylating and nitration are effected in a concatenated manner, without a necessity for interim isolation and purification of said 2,4-dihydroxypyridine, preferably by sequential heating of 2-hydroxy-3-cyano-4-methoxypyridine with concentrated phosphoric acid, then glacial acetic acid, then nitric acid.

A preferred embodiment of the invention is directed to a method for preparing the dihydrochloride salt of Compound IX comprising the steps of reacting Compound II with Compound III to form Compound IV, followed by replacing the hydroxyl moiety of Compound IV with a chloro group to form compound V, followed by reacting Compound V with Compound VI to form Compound VII, followed by reducing Compound VII to Compound VIII, followed by hydrolyzing Compound VIII, in the presence of hydrochloric acid, said steps being effected in a concatenated manner, without a necessity for interim isolation and purification of intermediate Compounds VIII, VII, V, or IV.

It will be apparent to one skilled in the art the hydroxypyridines may exist as the tautomer pyridinones, and that pyridinones may exist as tautomer hydroxypyridines. Accordingly, Compounds II, III, X, XI, and XII may exist in the form of the corresponding bydroxypyridine or pyridone, or as a mixture of the two forms.

The present invention is further explained, but is in no way limited by the following examples.

EXAMPLE 1

Preparation of [1S-[1a,2b,3b,4a(S*)]]-4-[7-[[1-(3-chloro-2-thienyl)methyl]propyl]amino]-3H-imidazo[4,5-b]pyridin-3-yl]-N-ethyl-2,3-dihydroxycyclopentanecarboxamide (Compound I)

[1S-[1a,2b,3b,4a(S*)]]-4-[[3-amino-4-[[1-[3-chloro-2-thienyl)methyl]propyl]amino]-2-pyridinyl]amino]-N-ethyl-2,3-dihydroxycyclopentanecarboxamide (Compound IX) dihydrochloride monohydrate (20 g) is suspended in water (120 ml) and the mixture heated to 65° C. to give a solution. Butyl acetate (84.7 g) is added, followed by sodium carbonate (15.2 g) in water (54 g). The mixture is stirred at 55±5° C. for about 10 minutes, then the layers are separated, and the organic layer washed with brine. To the organic layer is added formamidine acetate (10.3 g) and the mixture stirred at 85±5° C. for about 2 hours. The mixture is cooled to 55±° C., washed with 5% aqueous sodium bicarbonate solution, then water. Water (1.2 g) is added to the organic layer at 55±5° C., then the mixture is cooled to 21±2° C. over a period of about 2 hours. The mixture is stirred for 12 to 24 hours, filtered, the solid washed with butyl acetate, and dried in vacuo with a nitrogen bleed at 52° C. for about 24 hours to give [1S-[1a,2b,3b,4a(S*)]]-4-[7-[[1-(3-chloro-2-thienyl)methyl]propyl]amino]-3H-imidazo[4,5-b]pyridin-3-yl]-N-ethyl-2,3-dihydroxycyclopentanecarboxamide (Compound I) as a hydrate containing about 1.7% (w/w) water. $^1$HNMR (200 Mhz, DMSO) δ 0.915 (3H, t); 1.4 (3H, t); 3.2–3.0 (4H, m); 4.91 (1H, d); 6.3 (1H, d); 6.6 (1H, bd); 6.9 (1H, d); 7.4 (1H, d); 7.8 (1H, d); 8.05 (1H, bt); 8.2 (1H, s).

EXAMPLE 2

Preparation of [1S-[1a,2b,3b,4a(S*)]]4-[7-[[1-(3-chloro2-thienyl)methyl]propyl]amino]-3 H-imidazo[4,5-b]pyridin-3-yl]-N-ethyl-2,3-dihydroxycyclopentanecarboxamide (Compound I)

N-butyl acetate (54.3 g) and formamidine acetate (4.5 g, 43 mmol) are combined at room temperature. The mixture is heated to 100° C. and [1S-[1a,2b,3b,4a(S*)]]-4-[[3-amino-4-[[1-[3-chloro-2-thienyl)methyl]propyl]amino]-2-pyridinyl]amino]-N-ethyl-2,3-dihydroxycyclopentanecarboxamide (Compound IX) dihydrochloride monohydrate (8.4 g, 15 mmol) is added over 21 minutes. The mixture is stirred at 100 C. for 1 hour, then cooled to 80° C. and 8% W/W aqueous sodium bicarbonate (90 mL) is added. The mixture is stirred for 5 minutes and then the layers are separated. The organic layer (which is kept above 60° C.) is washed with water (45 g). The organic layer is then treated with activated charcoal (0.42 g) and stirred at 75° C. for 45 minutes. The reaction is filtered, and the filtrate cooled to 22° C. over a period of 1 hour. The mixture is stirred for 2 hours at 22° C., and the resulting solid filtered and washed with n- butyl acetate (6 mL). The collected white solid is dried under vacuum overnight at 50° C. with a nitrogen bleed to give Compound 1.

EXAMPLE 3

Preparation of [1S-[1a,2b,3b,4a(S*)]]-4-[7-[[1-(3-chloro-2-thienyl)methyl]propyl]amino]-3H-imidazo[4,5-b]pyridin-3-yl]-N-ethyl-2,3-dihydroxycyclopentanecarboxamide (Compound I)

N-butyl acetate (25.2 g) and formamidine acetate (2.81 g, 27 mmol) are combined at room temperature. The mixture is heated 100° C. and, at 94 to 100° C., and a room temperature slurry of Compound IX dihydrochloride monohydrate (8.4 g, 15 mmol) in n-butyl acetate (30.6 g) is added over 11 minutes, rinsing with n-butyl acetate (9.0 g) to complete the transfer of the slurry. The mixture is stirred at 100$_t$C. for 30 minutes. The reaction mixture is cooled to 80$_t$C and 8% W/W aqueous sodium bicarbonate (90 mL) is added. The mixture is stirred for 5 minutes then the layers are separated. The organic layer (which is kept above 60$_t$C) is washed with water (45 g). The organic layer is then treated with activated charcoal (0.42 g) and stirred at 75$_t$C for 45 minutes. The reaction is filtered, then cooled to 22$_t$C over 1 hour. The mixture is stirred for 2 hours at 22$_t$C, and the resulting solid collected by filtration, washed with n- butyl acetate (5 mL) to give Compound I.

EXAMPLE 4

Preparation of [3aR-[3aa,4a,6a(R*),6aa]]-6-[[3-amino4-[[I-[(3-chloro-2-thienyl)methyl]propyl]amino]-2-pyridinyl]amino]-N-ethyltetrahydro-2,2-dimethyl4H-cyclopenta-1,3-dioxole-4-carboxamide (Compound VIII)

[3aR-[3aa,4a,6a(R*),6aa]]-6-[[4-[[1-[(3-chloro-2-thienyl)methyl]propyl]amino]-3-nitro-2-pyridinyl]amino]-N-ethyltetrahydro-2,2-dimethyl-4H-cyclopenta-1,3-dioxole-4-carboxamide (Compound VII) (12.4 g), methanol (32.4 g), and 5% platinum on carbon (water wet, 62.4% assay) (9.6 g). The mixture is degassed with nitrogen and ammonium formate (10.0 g) is added. The mixture is heated at about 65° C. for 4 hours, cooled to 23° C., filtered through a filter aid (SulkaFloc 300), rinsing with ethyl acetate (180.4 g). The filtrate is washed with 5% aqueous sodium bicarbonate solution (50 mL), then half-saturated aqueous sodium chloride solution. The organic layer is evaporated in vacuo at 50° C. to give Compound VIII, as a foam which is used, without further treatment, for the next reaction.

EXAMPLE 5

Preparation of [1S-[1a,2b,3 b,4a(S*)]]4-[[3-amino-4-[[1-[3-chloro-2-thienyl)methyl]propyl]amino]-2-pyridinyl]amino]-N-ethyl-2,3-dihydroxycyclopentanecarboxamide (Compound IX)

Compound VIII (11.2 g) is combined with tetrahydrofuran (160 g) and concentrated hydrochloric acid (7.8 mL) is added over a period of 2 minutes. The mixture is stirred for 15 hours, then cooled to 0–3° C. and stirred for another 1 hour. The mixture is filtered, and the solid washed with cooled (0–3° C.) methyl t-butyl ether, then dried in vacuo at 55±5° C. with a nitrogen bleed for 48 hours to give Compound IX as the dihydrochloride monohydrate salt, m.p. 135° C.; MS (EI), m/z 467 (50%), $^1$HNMR (500 Mhz, DMSO) δ 0.91 (1H, t); 1.05 (1H t); 1.55 (2H, m); 2.39 (1H); 3.11 (1H); 4.01 (2H); 6.24 (1H) 6.36 (1H); 6.98 (1H); 7.37 (1H); 7.48 (1H); 12.47 (1H).

EXAMPLE 6

Preparation of (R)-N-[1-[(3-chloro-2-thienyl)methyl]propyl]-2-hydroxy-3-nitro-4-pyridinamine (Compound IV)

To a 3-neck 1 liter round bottom flask fitted with a mechanical stirrer, thermocouple, nitrogen inlet and a condenser is sequentially charged: 14.5 g of (R)-3-chloro-a-ethyl-2-thipheneethanamine (Compound III), 10.9 grams of 4-chloro-3-nitropyridin-2(1H)-one (Compound II), 35 grams of 2-propanol (IPA) and 25 mL of N,N-diisopropylethylamine (DIPEA). The mixture is stirred at 70° C.±2° C. for 7 hours before the reaction is allowed to cool overnight to room temperature (22° C±3° C.). The mixture is concentrated to 41. 4 g. of a syrup which is subsequently dissolved in 425 ml of ethyl acetate. This solution is washed with 125 mL of water, 2×50 mL of 5N ammonium chloride solution and 2×50 mL of saturated sodium chloride solution before drying over sodium sulfate. The solution is filtered, concentrated, and the resulting solid collected by filtration to give Compound IV, m.p. 150–152° C. Mass Spec. (EI), m/z 328 (6%), $^1$HNMR (500 Mhz, DMSO) δ 0.91 (3H, t); 1.8–1.6 (2H, m); 3.1 (1H, m); 3.95 (1H, m); 5.9 (1H, d); 7.0 (1H, d); 7.3 (1H, dd); 7.5 (1H, d); 8.8 (1H, d); 11.1 (1H).

EXAMPLE 7

Preparation of (R)-2-chloro-N-[1-[(3-chloro-2-thienyl)methyl]propyl]-3-nitro-4-pyridinamine (Compound V)

A toluene solution of (R)-N-[1-[(3-chloro-2-thienyl)methyl]propyl]-2-hydroxy-3-nitro4-pyridinamine (Compound IV) (0.1 mole in 100 mL of toluene) containing 2 equivalents of DIPEA hydrochloride is heated to 60° C. and 20.6 grams of phosphorous oxychloride is added over 10 minutes with stirring. The reaction is stirred at 60° C. until complete (3 hours). After cooling to 0° C., 245 grams of 2N sodium chloride is added at such a rate so as to maintain the reaction temperature below 10° C. The biphasic mixture is stirred 1–2 hours at 0° C. before it is allowed to warm to room temperature overnight. The bottom aqueous layer is separated from the organic layer. The organic layer is concentrated in vacuo and the residue purified by flash chromatography, eluting with 25:75 ethyl acetate:heptane, to give Compound V. MS (EI), m/z 345 (10%). $^1$HNMR (500 Mhz, CDCl$_3$/CD$_3$OD) δ 1.0 (3H, t); 1.5–1.8 (2H, m); 2.9–3.2 (2H, m); 3.8 (1H, m); 6.5 (1H, bd); 6.6 (1H, d ); 7.15 (1H, d); 7.9 (1H, d).

EXAMPLE 8

Preparation of [3aR-[3aa,4a,6a(R*),6aa]]-6-[[4-[[1-[(3-chloro2-thienyl)methyl]propyl]amino]-3-nitro-2-pyridinyl]amino]-N-ethyltetrahydro-2,2-dimethyl-4H-cyclopenta-1,3-dioxole4carboxamide (Compound VII)

To a toluene solution of (R)-2-chloro-N-[1-[(3-chloro-2-thienyl)methyl]propyl]-3-nitro-4-pyridinamine (Compound V) (0.1 mole in 100 mL of toluene) is successively added 28.5 grams of 325 mesh potassium carbonate followed by 33.7 grams of 2R,3S-isopropylidenedioxy-4R-amino-1S-ethylaminocarbonylcyclopentane (Compound VI) in single portions. The suspension is heated to 98° C.±2° C. for 6 hours. When the reaction is complete the suspension is cooled to room temperature and 230 grams of water is added with agitation. The aqueous layer is removed and a 1 4.5 w/w % ammonium chloride solution is charged to the organic layer with stirring before again removing the bottom aqueous layer. 100 grains of water is added and the layers are again separated. The toluene solution is concentrated in vacuo and the residue purified by flash chromatography, eluting with 60:40:5 ethyl acetate:heptane:triethylamine, to give Compound VII. Mass Spec. (FAB-LRP). (M+H)$^+$538 (100%), $^1$HNMR (500 Mhz, CDCl$_3$) δ 1.0 (3H, t), 1.15 (3H, t); 1.6 (1H, m); 1.75 (1H, m); 2.6 (1H, m); 2.8 (1H, m); 3.1, (2H, m); 3.35 (2H, m) 5.95 (1H, d); 6.85 (1H, d); 7.1 (1H, d); 7.8 (1H, d), 9.25 (1H, d); 9.55 (2H, d).

EXAMPLE 9

Preparation of [3aR-[3aa,4a,6a(R*),6aa]]-6-[[3-amino-4-[[1-[(3-chloro-2-thienyl)methyl]propyl]amino]-2-pyridinyl]amino]-N-ethyltetrahydro-2,2-dimethyl-4H-cyclopenta-1,3-dioxole-4-carboxamide (Compound VIII).

To a toluene solution of Compound VII (0.09 mole in 85 mL toluene) is charged 24 grams of methanol, 18 grams of IPA and 54 grams of ammonium acetate with stirring (15 min). 35 Grams of powdered zinc metal is then added in small portions (until no exotherm is observed) while maintaining the temperature of the reaction below 40° C. After the Zn addition is complete, the reaction mixture is stirred at 40° C. for 30 minutes before cooling the heterogeneous mixture to 0° C. The grey colored salts are filtered at 0° C. and washed with toluene. The filtrate is concentrated in vacuo and the residue purified by flash chromatography, eluting with 90:10:5 ethyl acetate:heptane:triethylamine to give Compound VIII. MS (M+H)$^+$508 (100%), $^1$HNMR (500 Mhz, DMSO) δ 0.9 (3H, t); 1.0 (3H, t); 1.7–1.4 (3H, m); 2.35 (1H, m); 2.95 (2H, m); 3.1, (2H, m); 5.75 (1H, d) 6.0 (1H, d); 7.0(1H, d); 7.25 (1H, d); 8.15 (1H, m).

EXAMPLE 10

Concatenated preparation of [1S-[1a,2b,3b,4a(S*)]]-4-[[3-amino-4-[[1-[3-chloro-2-thienyl)methyl]propyl]amino]-2-pyidinyl]amino]-N-ethyl-2,3-dihydroxycyclopentanecarboxamide (Compound IX).

To a 3-neck 1 liter round bottom flask fitted with a mechanical stirrer, thermocouple, nitrogen inlet and a condenser is sequentially charged: 23.3 grams of (R)-3-chloro-a-ethyl-2-thiopheneethanamine (Compound III) hydrochloride, 18.0 grams of 4-chloro-3-nitropyridin-2 (1H)-one (Compound II), 35 grams of 2-propanol (IPA) and and 33.3 g of N,N-diisopropylethylamine (DIPEA). The mixture is stirred while heating the batch to 70° C.±2° C. for 5 to 7 hours. The reaction is allowed to cool overnight to room temperature (22° C.±3° C.). In the morning 240 grams of toluene is added to the reaction vessel and IPA/toluene is azeotropically removed by distillation at 80–90° C. and reduced pressure. Residual IPA is monitored by gas chromatography.

When the level of IPA is below 0.1%, the resulting liquid/liquid biphasic mixture containing (R)-N-[1-[(3-chloro-2-thienyl)methyl]propyl]-2-hydroxy-3-nitro-4-pyridinamine (Compound IV) is cooled to 60° C. and 20.6 grams of phosphorous oxychloride is added over 10 minutes with stirring. The reaction is stirred at 60° C. until reaction is complete (2–3 hours) before cooling to 0° C. and adding 245 grams of 2N aqueous sodium hydroxide solution at such a rate so as to maintain the reaction temperature below 10° C. The biphasic mixture is stirred 1–2 hours at 0° C. before it is allowed to warm to room temperature overnight.

In the morning, the bottom aqueous layer is separated from the organic layer containing (R)2-chloro-N-[1-[(3-chloro-2-thienyl)methyl]propyl]-3-nitro-4-pyridinamine (Compound V) and 28.5 grams of 325 mesh potassium carbonate followed by 33.7 grams of 2R,3S-isopropylidenedioxy4R-amino-1S-ethylaminocarbonylcyclopentane (Compound VI) are added to the organic layer in single portions. The suspension is heated to 98° C.±2° C. for 2–6 hours. When the reaction is complete, 230 grams of deionized water is added with agitation. The aqueous layer is removed and a 14.5 w/w % aqueous ammonium chloride solution is charged to the organic layer with stirring before again removing the bottom aqueous layer. 100 grams of deionized water is added and the layers are again separated.

To the toluene solution of [3aR-[3aa,4a,6a(R*),6aa]]-6-[[4-[[1-[(3-chloro-2-thienyl)methyl]propyl]amino]-3-nitro-2-pyridinyl]amino]-N-ethyltetrahydro-2,2-dimethyl-4H-cyclopenta-1,3-dioxole-4-carboxamide (Compound VII) is charged 24 grams of methanol, 18 grams of IPA and 54 grams of ammonium acetate with stirring (15 min). 35 grams of powdered zinc metal is then added in small portions (until no exotherm is observed) while maintaining the temperature of the reaction below 40° C. After the Zn addition is complete, the reaction mixture is stirred at 40° C. for 30 minutes before cooling the heterogeneous mixture to 0° C. The grey colored salts were filtered and washed with toluene. The filtrate (a toluene solution of [3aR-[3aa,4a,6a(R*), 6aa]]-6-[[3-amino-4-[[1-[(3-chloro-2-thienyl)methyl]propyl] amino]-2-pyridinyl]amino]-N-ethyltetrahydro-2,2-dimethyl-4H-cyclopenta-1,3-dioxole-4-carboxamide (Compound VIII)) is used directly in the next reaction.

To the toluene solution of Compound VIII is added 100 grams of IPA and the mixture agitated while warming to 50±3° C. 31 grams of concentrated hydrochloric acid was added slowly over several minutes. When the consumption of Compound VIII is complete, the reaction temperature is lowered to 22° C.±3° C. and agitated overnight. In the morning, the suspension is cooled to 0° C. and 45 grams of ethyl acetate is added. After stirring at this temperature for 1 hour, the solids are filtered and washed sequentially with cold (0° C.) IPA and room temperature ethyl acetate. The off white filtercake is dried at 40° C.±3° C. under vacuum for 10 hours to yield [1S-[1a,2b,3b,4a(S*)]]-4-[[3-amino-4-[[1-[3-chloro-2-thienyl)methyl]propyl]amino]-2-pyridinyl] amino]-N-ethyl-2,3-dihydroxycyclopentanecarboxamide as the dihydrochloride, monohydrate. Melting point: 135° C.

EXAMPLE 11

Preparation of 4-chloro-3-nitropyridin-2(1H)-one (Compound II)

A 150 mL flask is charged with 2,4-dihydroxy-3-nitropyridine (Compound XII) (10.0 g, 0.064 mole), and toluene (30 mL). The mixture is stirred at moderate speed and warmed to 47° C. Phosphorus oxychloride (POCl$_3$) (4.4 g, 0.0289 moles) is added over 10 minutes, via a syringe pump, giving an exotherm to 49° C. N,N-diisopropylethylamine (DIPEA )(2.22 g, 0.017 moles) is added over 10 minutes, giving an exotherm to 51° C. Another portion of POCl$_3$ (4.4 g, 0.0289 moles) is added over 10 minutes, followed by another portion of DIPEA (2.22 g, 0.017 moles) over 10 minutes. A third portion of POCl$_3$ (4.4 g, 0.0289 moles) is added over 10 minutes, followed by a third portion of DIPEA (2.22 g, 0.017 moles) over 10 minutes, followed by a final portion of POCl$_3$ (4.4g, 0.0289 moles) over 10 minutes (total POCl$_3$ added is 17.7 g), then by a final portion of DIPEA (2.22 g, 0.017 moles) over 10 min.(total DIPEA added is 8.9 g). The reaction is then stirred at 50° C. for 5 hr until IPC indicates complete consumption of Compound XII. The reaction is allowed to cool to 20° C. over 30 minutes and 50 mL of water is added over 1.5 hr allowing the temperature to rise to 47° C. This mixture is stirred for four hours while cooling to 25° C. The batch is filtered washing twice with 15 mL of water, then twice with 15 mL of toluene. The product is dried to give Compound II.

EXAMPLE 12

Preparation of 2,4-dihydroxy-3-nitropyridine (Compound XII)

86% phosporic acid (90 mL, 151.3 g) and 3-cyano-4-methoxy-2(1H)-pyridinone (Compound X) (30.0 g, 0.20 mole) are combined under argon in a 500 mL flask equipped with a mechanical stirrer, reflux condensor. The mixture is heated in an oil bath at 175–180° C. for 23 hours. The reaction mixture is cooled to 71° C. and glacial acetic acid (90 mL, 94.5 g) added and the mixture heated at 90° C. for about 90 minutes. Fuming nitric acid (density=1.52) (12.6 g, 8.3 ml) is then added carefully over a period of 15 minutes (giving a mild exotherm), and the mixture heated at 90–95° C. for 2 hours. Water (90 mL) is then added to the mixture and heating at 90° C. continued for 1 hour. The mixture is then cooled slowly with stirring to room temperature, filtered through a sintered glass funnel and the residue washed with water to give Compound XII, m.p. 268° C.; NMR (DMSO) δ 7.44 (1H, d); 6.0 (1H, d); 3.5 (2H).

EXAMPLE 13

Preparation of [1S-[1a,2b,3b,4a(S*)]]-4-[[3-amino-4-[[1-[3-chloro-2-thienyl)methyl]propyl]amino]-2-pyridinyl]amino]-N-ethyl-2,3-dihydroxycyclopentanecarboxamide (Compound IX)

To a 3-neck round bottom flask blanketed under nitrogen is sequentially charged 5% Pt/C (Degussa type F101 RA/W, 21.6 grams, 2.71 mmol), ammonium formate (34 grams, 543 mmol), an ethyl acetate solution of Compound VII (10 mL containing 29 grams of Compound VII, 54.3 mmol) and methanol (66 grams) with mechanical agitation. The black suspension is heated at 60° C. for 6 hours, cooled to ambient temperature and filtered through Celite to remove the insoluble species. The filter cake is washed with 2×50 mL of ethyl acetate. To the combined filtrates is added concentrated hydrochloric acid (40 mL) over several minutes with agitation and the mixture is stirred for 3 hours at ambient temperature. Filtration followed by drying at 50° C. in a vacuum oven yields Compound IX as the dihydrochloride monohydrate as an off white solid.

EXAMPLE 14

Preparation of [[1S-[1a,2b,3b,4a(S*)]]-4-[(3-amino4-[[1-[3-chloro-2-thienyl)methyl]propyl]amino]-2-pyridinyl]amino]-N-ethyl-2,3-dihydroxycyclopentanecarboxamide (Compound IX)

To a 500 ml Paar bottle is charged 1.8 g. of 5% Pt on carbon (Aldrich, wet, Degussa F101 RA/W) and a toluene solution of Compound VII (8.9 grams 16.6 moles in 50 grams of toluene). The mixture is shaken under a hydrogen pressure of 52 PSI for 15 hours at ambient temperature. The black slurry is filtered through Celite to give a solution of Compound VIII. To this solution at 20° C., 2-propanol (20 grams), toluene (57 grams) and concentrated hydrochloric acid (7.4 grams) are added in succession and the solution is warmed to 45° C. with mechanical agitation. After 2 hours at this temperature the tan precipitate is filtered and washed with 20 ml of 2-propanol. The filter cake is dried for 6 hours at 45° C. to give Compound IX as the dihydrochloride monohydrate.

EXAMPLE 15

Preparation of [1S-[1a,2b,3b,4a(S*)]]-4-[7-[[1-(3-chloro-2-thienyl)methyl]propyl]amino]-3H-imidazo[4,5-b]pyridin-3-yl]-N-ethyl-2,3-dihydroxycyclopentanecarboxamide (Compound I)

In a 3- neck round bottom flask fitted with a condenser and a magnetic stir bar is sequentially added Compound IX, as the dihydrochloride monohydrate (2.2 g, 3.9 mmol) and deionized water (12 grams). The suspension is heated to 65° C. and an aqueous solution of sodium carbonate (1.7 g Na$_2$CO$_3$ in 5 grams deionized water, warmed to 65° C.) is added. The organic phase separates out as a light tan oil. Triethylorthoformate (6.8 mL, 41 mmol) is then added to the biphasic mixture and the lower aqueous layer is removed. After the addition of concentrated HCl (90 ul), the solution is heated for 5 hours at 80° C. The solution is cooled to 70° C., n-butyl acetate (10 mL) is added and the organic layer is washed with saturated sodium carbonate followed by water and brine. The organic layer is cooled to ambient temperature and stirred for 16 hours. Filtration followed by drying at 50° C. in a vacuum oven yields Compound I.

EXAMPLE 16

Preparation of [1S-[1a,2b,3b,4a(S*)]]4-[7-[[1-(3-chloro-2-thienyl)methyl]propyl]amino]-3H-imidazo[4,5-b]pyridin-3-yl]-N-ethyl-2,3-dihydroxycyclopentanecarboxamide (Compound I)

In a 3-neck round bottom flask fitted with a condensor and a magnetic stir bar is sequentially added Compound IX as the dihydrochloride monohydrate (2.0 g, 3.6 mmol) and deionized water (12 grams). The suspension is heated to 65° C. and an aqueous solution of sodium carbonate (1.6 g Na$_2$CO$_3$ in 5 grams deionized water, warmed to 65° C.) is added. Triethylorthoformate (9.0 mL, 54.3 mmol) is then added to the biphasic mixture and the lower aqueous layer was removed. The organic layer is washed with deionized water (5 mL) and the lower layer is again removed. After the addition of (1R)-(–)-10-camphorsulfonic acid (42 mg, 0.18 mmol), the solution is heated for 2 hours at 80° C. and 15 hours at 25° C. The reaction mixture is warmed back to 70° C., n-butyl acetate (10 mL) is added and the organic layer is washed with saturated sodium carbonate followed by water and brine. The organic layer is cooled to ambient temperature and stirred for 16 hours. Filtration followed by drying at 50° C. in a vacuum oven gives Compound I.

EXAMPLE 17

Preparation of [1S-[1a,2b,3b,4a(S*)]]4-[7-[[1-(3-chloro-2-thienyl)methyl]propyl]amino]-3H-imidazo[4,5-b]pyridin-3-yl]-N-ethyl-2,3-dihydroxycyclopentanecarboxamide (Compound I)

To a 250 mL 3 neck round bottom flask fitted with a mechanical stirrer, thermocouple, nitrogen inlet and a condenser is sequentially charged at 22° C.: 8.4 g of Compound IX as the dihydrochloride monohydrate, 54.3 g of n-butyl acetate and 4.5 g of formamidine acetate. The suspension is stirred while heating at 90° C. for 2 to 4 hours. Upon completion of the reaction (disappearance of Compound IX) the reaction mixture is cooled to 60° C. and washed with a dilute solution of warm sodium bicarbonate followed by 45 grams of warn water. After removing the aqueous layers, the organic solution is treated with 400 mg of activated charcoal and 0.5 g water and heated to 70° C. with agitation for 45 minutes. The hot suspension is filtered and the filtrate is cooled to room temperature and stirred for an additional 2 hours at 22° C. The resulting solid is collected by filtration, washed with butyl acetate, and dried in a vacuum oven at 50° C.

One skilled in the art will readily appreciate that the present invention is well adapted to carry out the objects of the invention, and obtain the ends and advantages mentioned, as well as those inherent therein. The compounds and methods described herein are presented as representative of the preferred embodiments, or intended to be exemplary and not intended as limitations on the scope of the present invention.

What is claimed is:

1. A method for preparing 4-hydroxy-3-nitro-2(1H)-pyridone comprising hydrolyzing and decarboxylating 2-hydroxy-3-cyano-4-methoxy pyridine to give 2,4- dihydroxypyridine, followed by nitration of said 2,4-dihydroxypyridine.

2. A method according to claim 1 wherein said hydrolyzing, decarboxylating and nitration are effected in a concatenated manner, without a necessity for interim isolation and purification of said 2,4-dihydroxypyridine.

\* \* \* \* \*